(12) United States Patent
Gomi et al.

(10) Patent No.: US 9,517,029 B2
(45) Date of Patent: Dec. 13, 2016

(54) IMAGE PROCESSING DEVICE, IMAGE PROCESSING METHOD, IMAGE PROCESSING SYSTEM, PROGRAM, AND RECORDING MEDIUM

(75) Inventors: Shinichiro Gomi, Tokyo (JP); Masaru Suzuki, Tokyo (JP); Yusuke Nakamura, Chiba (JP); Hideo Sato, Tokyo (JP); Kazuo Omori, Kanagawa (JP); Mitsuharu Ohki, Tokyo (JP)

(73) Assignee: Sony Corporation (JP)

( * ) Notice: Subject to any disclaimer, the term of this patent is extended or adjusted under 35 U.S.C. 154(b) by 471 days.

(21) Appl. No.: 13/483,446

(22) Filed: May 30, 2012

(65) Prior Publication Data

US 2012/0307032 A1    Dec. 6, 2012

(30) Foreign Application Priority Data

Jun. 6, 2011 (JP) .................................. 2011-126021

(51) Int. Cl.
| | | |
|---|---|---|
| *A61B 5/00* | (2006.01) | |
| *A61B 5/103* | (2006.01) | |
| *G06T 7/40* | (2006.01) | |
| *G06F 19/00* | (2011.01) | |

(52) U.S. Cl.
CPC .............. *A61B 5/441* (2013.01); *A61B 5/0077* (2013.01); *A61B 5/103* (2013.01); *G06T 7/403* (2013.01); *G06F 19/321* (2013.01); *G06T 2207/10148* (2013.01); *G06T 2207/10152* (2013.01); *G06T 2207/20081* (2013.01); *G06T 2207/30088* (2013.01); *G06T 2207/30201* (2013.01)

(58) Field of Classification Search
CPC ........... H04N 1/047; H04N 1/192; G06K 1/00
USPC .............................................. 348/77; 382/128
See application file for complete search history.

(56) References Cited

U.S. PATENT DOCUMENTS

| | | | |
|---|---|---|---|
| 8,718,336 B2 * | 5/2014 | Yamaguchi ............. | G06T 5/005 382/118 |
| 2004/0207743 A1 * | 10/2004 | Nozaki ............... | H04N 5/23212 348/333.12 |
| 2007/0064985 A1 | 3/2007 | Chhibber et al. | |
| 2009/0196475 A1 | 8/2009 | Demirli et al. | |
| 2009/0245603 A1 * | 10/2009 | Koruga .................. | A45D 44/00 382/128 |
| 2010/0097485 A1 * | 4/2010 | Lee ........................ | G06T 7/0012 348/222.1 |
| 2010/0185064 A1 | 7/2010 | Bandic et al. | |
| 2010/0284610 A1 * | 11/2010 | Yoshikawa ................... | 382/164 |

FOREIGN PATENT DOCUMENTS

| | | |
|---|---|---|
| WO | 2006-064635 A1 | 6/2006 |
| WO | 2010111463 A1 | 9/2010 |

OTHER PUBLICATIONS

European Search Report EP 12169199, dated Oct. 24, 2012.

* cited by examiner

*Primary Examiner* — William C Vaughn, Jr.
*Assistant Examiner* — Jerry Jean Baptiste
(74) *Attorney, Agent, or Firm* — Lerner, David, Littenberg, Krumholz & Mentlik, LLP

(57) ABSTRACT

Provided is an image processing device including a specifying unit configured to specify a part of a living body within a first image on the basis of a characteristic amount of the first image capturing skin of the living body, and a setting unit configured to set a capturing condition under which a second image indicating a state of the skin of the part is captured in response to the specified part.

9 Claims, 20 Drawing Sheets

FIG.8

| TARGET PART | WAVELENGTH | MEASUREMENT DEPTH | POLARIZATION DIRECTION | CAPTURING RANGE | MEASUREMENT ITEM |
|---|---|---|---|---|---|
| CHEEKS | WHITE LIGHT | 0mm | PARALLEL | 1cm×1cm | TEXTURE |
| NOSE | UV LIGHT(390nm) | 0mm | — | 1cm×1cm | KERATIN PLUG |
| BACK OF HAND | UV LIGHT(390nm) | 0mm | ORTHOGONAL | 3cm×3cm | SPOT |
| FOREHEAD | WHITE LIGHT | 0mm | PARALLEL | 5cm×5cm | WRINKLE |

FIG.19

| TARGET PART | WAVELENGTH | MEASUREMENT DEPTH | POLARIZATION DIRECTION | CAPTURING RANGE | MEASUREMENT ITEM |
|---|---|---|---|---|---|
| CHEEKS | UV LIGHT(390nm) | 0.2mm | ORTHOGONAL | 1cm×1cm | SPOT |
| NOSE | UV LIGHT(390nm) | 0mm | — | 1cm×1cm | KERATIN PLUG |
| BACK OF HAND | UV LIGHT(390nm) | 0mm | ORTHOGONAL | 3cm×3cm | SPOT |
| FOREHEAD | WHITE LIGHT | 0mm | PARALLEL | 5cm×5cm | WRINKLE |

IMAGE PROCESSING DEVICE, IMAGE PROCESSING METHOD, IMAGE PROCESSING SYSTEM, PROGRAM, AND RECORDING MEDIUM

CROSS-REFERENCE TO RELATED APPLICATION

The present application claims priority from Japanese Patent Application No. JP 2011-126021 filed in the Japanese Patent Office on Jun. 6, 2011, the entire content of which is incorporated herein by reference.

BACKGROUND

The present technology relates to an image processing device, an image processing method, an image processing system, a program, and a recording medium, and in particular, to an image processing device, an image processing method, an image processing system, a program, and a recording medium that are suitable to measure a state of skin.

Typically, devices that measure the state of skin on the basis of an image capturing the skin have been proposed.

For example, a diagnosis system that irradiates a plurality of illumination lights having different wavelengths on a part of a subject to be diagnosed and determines a healthy state and an abnormal state on the basis of spectral reflectances of the respective wavelengths on the part is proposed (see International Publication No. 2006/064635).

SUMMARY

It is desired to be able to simply and correctly recognize the state of the skin through the technique of measuring the state of the skin.

The present technology enables the state of the skin to be simply and correctly recognized.

According to a first aspect of the present technology, there is provided an image processing device which includes a specifying unit configured to specify a part of a living body within a first image on the basis of a characteristic amount of the first image capturing skin of the living body, and a setting unit configured to set a capturing condition under which a second image indicating a state of the skin of the part is captured in response to the specified part.

The image processing device may further include a measurement unit configured to measure the state of the skin of the specified part on the basis of the second image captured under the set capturing condition.

The measurement unit may measure at least one of texture, a wrinkle, a spot, and a keratin plug of the skin in the specified part.

The image processing device may further include a display control unit configured to control display of a measurement result of the part.

The setting unit may set at least one of a wavelength of light used to capture the second image, a depth of a focus location from a surface of the part, a relationship between a polarization direction of illumination light and a polarization direction of incident light incident on an image sensor, and a capturing magnification on the basis of at least one of the part and measurement items in the part.

The image processing device may further include a characteristic analysis unit configured to extract a characteristic amount of the first image. The specifying unit may specify the part of the living body within the first image on the basis of the characteristic amount extracted by the characteristic analysis unit.

The image processing device may further include a learning unit configured to learn identification information for identifying the part of the living body on the basis of the characteristic amount. The specifying unit may specify the part of the living body within the first image on the basis of the characteristic amount extracted by the characteristic analysis unit and the identification information learned by the learning unit.

The image processing device may further include a capturing unit configured to capture the living body.

According to a first aspect of the present technology, there is provided an image processing method which includes, by an image processing device, specifying a part of a living body within a first image on the basis of a characteristic amount of the first image capturing skin of the living body, and setting a capturing condition under which a second image indicating a state of the skin of the part is captured in response to the specified part.

According to a first aspect of the present technology, there is provided a program which causes a computer to execute processes including specifying a part of a living body within a first image on the basis of a characteristic amount of the first image capturing skin of the living body, and setting a capturing condition under which a second image indicating a state of the skin of the part is captured in response to the specified part.

According to a second aspect of the present technology, there is provided an image processing system which includes a capturing device and an image processing device, and the image processing device includes a specifying unit configured to specify a part of a living body within a first image on the basis of a characteristic amount of the first image of skin of the living body captured by the capturing device, and a setting unit configured to set, on the capturing device, a capturing condition under which a second image indicating a state of the skin of the part is captured in response to the specified part.

According to the first aspect of the present technology, a part of a living body within a first image is specified on the basis of a characteristic amount of the first image capturing skin of the living body, and a capturing condition under which a second image indicating a state of the skin of the part is captured in response to the specified part is set.

According to the second aspect of the present technology, a part of a living body within a first image is specified on the basis of a characteristic amount of the first image capturing skin of the living body, and a capturing condition under which a second image indicating a state of the skin of the part is captured in response to the specified part is set on the capturing device.

According to the first or second aspect of the present technology, the skin state can be simply and correctly recognized.

BRIEF DESCRIPTION OF THE DRAWINGS

FIG. 8 is a diagram illustrating a first example of a measurement condition setting table;

FIG. 19 is a diagram illustrating a second example of a measurement condition setting table;

DETAILED DESCRIPTION OF THE EMBODIMENT(S)

Hereinafter, forms for embodying the present technology (hereinafter, referred to as embodiments) will be described. In addition, the description will be made in the following order.

1. Embodiments
2. Modifications

1. Embodiments

Configuration Example of Image Processing System 1

Figure 1:
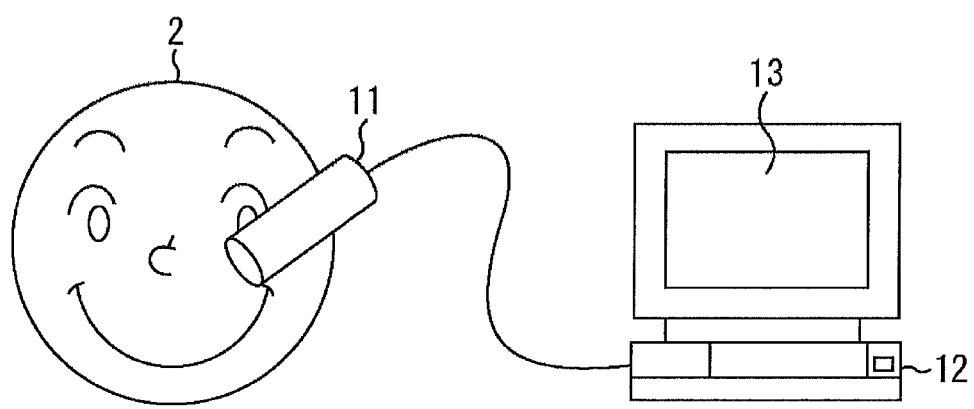
FIG. 1 is a block diagram illustrating a first embodiment of an image processing system to which the present technology is applied.

FIG. 1 is a block diagram illustrating a first embodiment of an image processing system 1 to which the present technology is applied.

The image processing system 1, for example, is a system that captures a part of a subject 2 such as cheeks, a nose, a forehead, and a back of the hand (hereinafter referred to as a target part), and measures a state of skin of the target part of the subject 2 and analyzes the measurement result (e.g., processes various statistics and so forth) on the basis of the captured image (hereinafter referred to as a part image). In addition, the image processing system 1 measures and analyzes not only the state of the skin surface but also a state inside the skin in which the spot or the like is present and on which the spot or the like appears in the future, for example.

The image processing system 1 includes a capturing device 11, an image processing device 12, and a display device 13. The capturing device 11 and the image processing device 12 perform wired or wireless communication. In addition, communication methods between the capturing device 11 and the image processing device 12 are not limited to a specific method but any communication methods including the wired or wireless communication method may be employed. In FIG. 1, it is illustrated that the capturing device 11 and the image processing device 12 are connected by a cable to perform wired communication.

Configuration Example of Capturing Device 11

Figure 2:
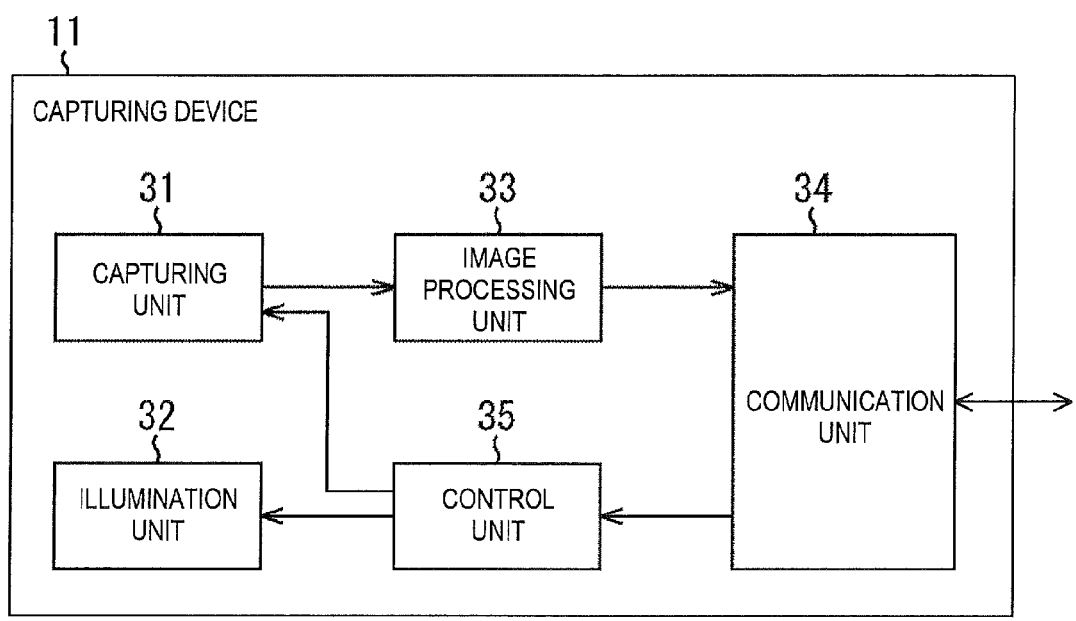
FIG. 2 is a block diagram illustrating a configuration example of functions of a capturing device.

FIG. 2 is a block diagram illustrating a configuration example of the capturing device 11.

The capturing device 11 includes a capturing unit 31, an illumination unit 32, an image processing unit 33, a communication unit 34, and a control unit 35.

The capturing unit 31 has an image sensor and so forth, captures the skin of the subject, and supplies the obtained part image to the image processing unit 33 under control of the control unit 35. In addition, the capturing unit 31 has an image sensor capable of capturing light in a wavelength band ranging at least from visible light to UV light.

The illumination unit 32 irradiates illumination light on a region including the target part of the subject captured by the capturing unit 31 under control of the control unit 35. In addition, a specific example of the configuration of the illumination unit 32 will be described later with reference to FIG. 9.

The image processing unit 33 performs a predetermined image process such as noise removal on the part image and supplies the processed result to the communication unit 34.

The communication unit 34 is in communication with the image processing device 12 using a predetermined communication method. The communication unit 34 then transmits the part image to the image processing device 12. In addition, the communication unit 34 receives capturing condition setting information transmitted from the image processing device 12 and supplies the capturing condition setting information to the control unit 35.

The control unit 35 sets the capturing condition of the part image for the capturing unit 31 and the illumination unit 32 on the basis of the capturing condition setting information while controlling the capturing unit 31 and the illumination unit 32.

Configuration Example of Image Processing Device 12

Figure 3:
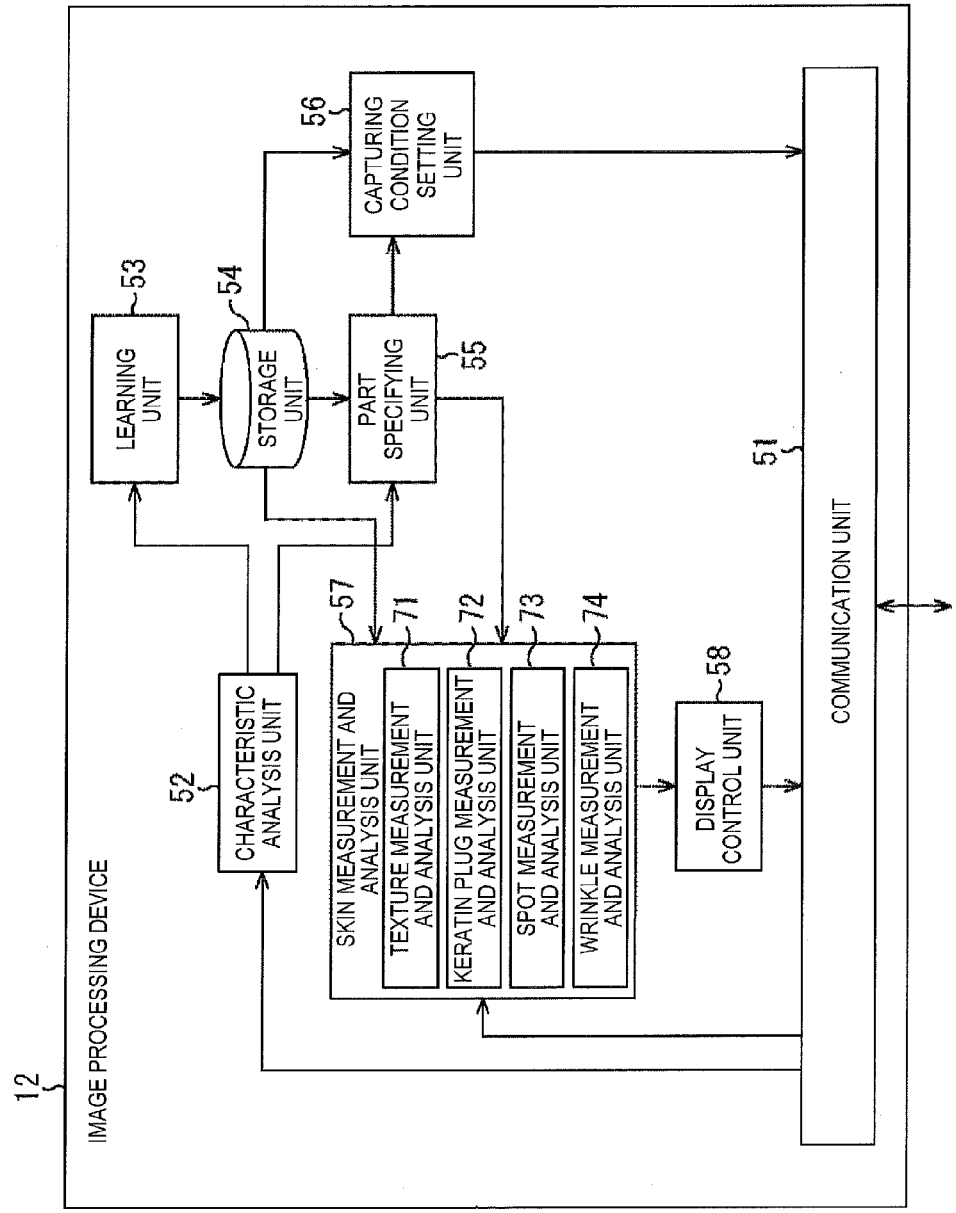
FIG. 3 is a block diagram illustrating a configuration example of functions of an image processing device.

FIG. 3 is a block diagram illustrating a configuration example of functions of the image processing device 12.

The image processing device 12 includes a communication unit 51, a characteristic analysis unit 52, a learning unit 53, a storage unit 54, a part specifying unit 55, a capturing condition setting unit 56, a skin measurement and analysis unit 57, and a display control unit 58. In addition, the skin measurement and analysis unit 57 includes a texture measurement and analysis unit 71, a keratin plug measurement and analysis unit 72, a spot measurement and analysis unit 73, and a wrinkle measurement and analysis unit 74.

The communication unit 51 is in communication with the capturing device 11 using a predetermined communication method.

The characteristic analysis unit 52 receives the part image from the capturing device 11 through the communication unit 51. The characteristic analysis unit 52 analyzes the characteristic of the part image and extracts the characteristic amount of the part image as will be described below. The characteristic analysis unit 52 supplies information indicating the extracted characteristic amount of the part image to the learning unit 53 or the part specifying unit 55.

The learning unit 53 learns identification information used to identify the part of the subject reflected in the part image based on the characteristic amount on the basis of the information indicating the characteristic amount of the part image supplied from the characteristic analysis unit 52 and correct data given from the outside as will be described below. The learning unit 53 causes learning data for generating the identification information, and identification information obtained from the learning to be stored in the storage unit 54.

The storage unit 54 stores a measurement condition setting table in addition to the learning data and the identification information described above. The measurement condition setting table acts to set the capturing condition, the measurement items, and so forth of the part image that are used to measure the skin state of the target part. For example, the measurement condition setting table is created by a user or provided by a manufacturer, a seller, and so forth of the image processing system 1.

In addition, a specific example of the measurement condition setting table will be described below with reference to FIG. 8 and so forth.

The part specifying unit 55 specifies a part (target part) of the subject within the part image on the basis of the characteristic amount extracted from the part image by the characteristic analysis unit 52 and the identification information stored in the storage unit 54. The part specifying unit 55 notifies the capturing condition setting unit 56 and the skin measurement and analysis unit 57 of the specified target part.

The capturing condition setting unit 56 sets the capturing condition of the capturing device on the basis of the target part specified by the part specifying unit 55 and the measurement condition setting table stored in the storage unit 54. The capturing condition setting unit 56 then transmits capturing condition setting information indicating the set capturing condition to the capturing device 11 through the communication unit 51.

The skin measurement and analysis unit 57 receives the part image from the capturing device 11 through the communication unit 51. The skin measurement and analysis unit 57 specifies the item to be measured in the target part on the basis of the target part specified by the part specifying unit 55 and the measurement condition setting table stored in the storage unit 54. In addition, the skin measurement and analysis unit 57 measures the item to be measured in the target part on the basis of the part image and also analyzes the measurement result. The skin measurement and analysis unit 57 then supplies the results of measurement and analysis of the target part and the part image (hereinafter referred to as a measurement and analysis result) to the display control unit 58.

In addition, the items to be measured include, for example, texture, a keratin plug, a spot, and a wrinkle. The texture measurement and analysis unit 71, the keratin plug measurement and analysis unit 72, the spot measurement and analysis unit 73, and the wrinkle measurement and analysis unit 74 measure states of the texture, the keratin plug, the spot, and the wrinkle in the target part on the basis of the part image, and analyze the measurement results, respectively.

The display control unit 58 generates data indicating the measurement and analysis result of the skin state of the target part on the basis of the part image and the measurement and analysis result, and supplies the data to the display device 13.

Configuration Example of Characteristic Analysis Unit 52

Figure 4:
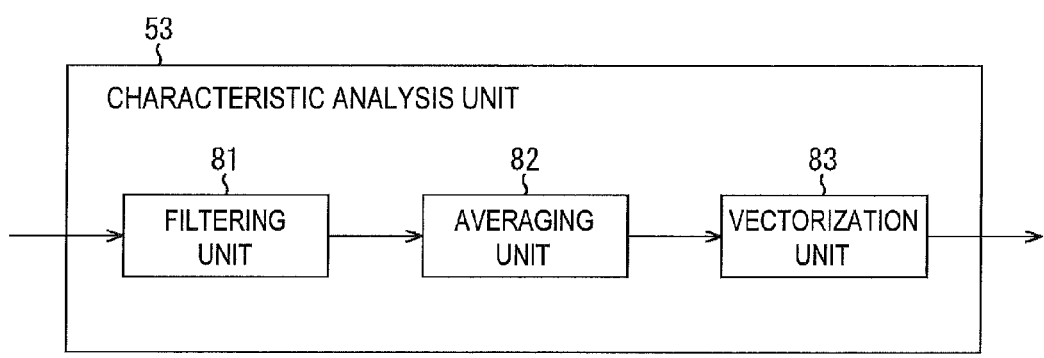
FIG. 4 is a block diagram illustrating a configuration example of functions of a characteristic analysis unit.

FIG. 4 is a block diagram illustrating a configuration example of functions of the characteristic analysis unit 52.

The characteristic analysis unit 52 includes a filtering unit 81, an averaging unit 82, and a vectorization unit 83.

The filtering unit 81 applies a plurality of Gabor filters of different parameters as will be described below. The filtering unit 81 then supplies a plurality of obtained images to the averaging unit 82.

The averaging unit 82 divides each of the images into small blocks, and calculates an average value of pixel values per small block. The averaging unit 82 supplies the calculated averages to the vectorization unit 83.

The vectorization unit 83 generates the vector including the average values supplied from the averaging unit 82 as a characteristic amount vector indicating the characteristic amount of the part image. The vectorization unit 83 supplies the generated characteristic amount vector to the learning unit 53 or the part specifying unit 55.

Next, processes of the image processing system 1 will be described with reference to FIGS. 5 to 20.

Learning Process

First, the learning process carried out by the image processing system 1 will be described with reference to the flowchart of FIG. 5.

In addition, for example, this process is initiated when an instruction to initiate the learning process is input to the image processing system 1 through an input unit not shown.

In step S1, the image processing system 1 captures the part image. In particular, a user captures at least one of cheeks, a nose, a forehead, and a back of the hand of the subject using the capturing device 11. In addition, the user (capturer) and the subject may be the same person or may not be the same person.

The capturing unit 31 then supplies the captured part image to the image processing unit 33.

The image processing unit 33 performs the image process such as noise removal on the part image and also cuts out a predetermined region of a central portion of the part image. In addition, hereinafter, it is considered that the region of 128×128 pixels of the central portion of the part image is cut out. The image processing unit 33 supplies the part image subjected to the image process to the communication unit 34.

The communication unit 34 transmits the part image to the image processing device 12.

The communication unit 51 of the image processing device 12 receives the part image transmitted from the capturing device 11, and supplies the part image to the filtering unit 81 of the characteristic analysis unit 52.

In step S2, the characteristic analysis unit 52 analyzes the characteristic of the part image.

In particular, the filtering unit 81 of the characteristic analysis unit 52 applies the Gabor filter to the part image by carrying out an operation as in equation (1) below.

$$g(x, y) = \exp\left(-\frac{x'^2 + \gamma^2 y'^2}{2\sigma^2}\right)\cos\left(2\pi\frac{x'}{\lambda} + \Psi\right) \quad (1)$$

In addition, g(x, y) indicates the pixel value of the coordinates (x, y) of the image subjected to the Gabor filter. In addition, x' and y' are expressed as in equations (2) and (3) below using the x and y coordinates of the part image.

$$x' = x' \cos\theta + y \cdot \sin e \quad (2)$$

$$y' = -x' \sin\theta + y' \cos\theta \quad (3)$$

In addition, λ indicates a cosine component of the wavelength, θ indicates a direction of a striped pattern of the Gabor function, ψ indicates a phase offset, σ indicates a scale, and γ indicates a spatial aspect ratio.

In this case, for example, the filtering unit 81 selects θ from four kinds such as 0°, 45°, 90°, and 135° and σ from two kinds such as 1.0 and 5.0 as parameters of the Gabor filter, and applies eight kinds of the Gabor filter as a total combination of θ and σ. Eight result images are thus generated from the part image. The filtering unit 81 supplies the generated eight result images to the averaging unit 82.

Figure 6:
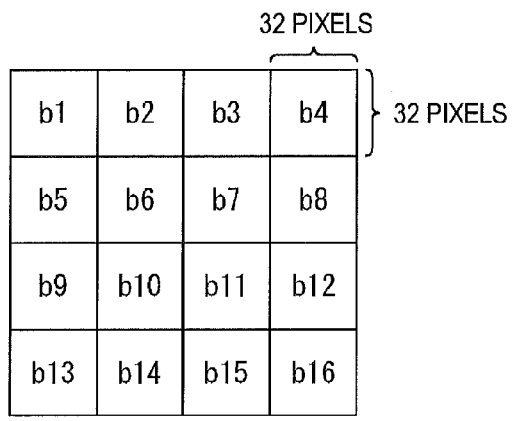
FIG. 6 is a diagram illustrating a method of generating a characteristic amount vector.

The averaging unit 82 divides each of the result images into sixteen small blocks b1 to b16 each having 32×32 pixels as shown in FIG. 6, and obtains an average value of the pixel values of each small block. As a result, 128 average values of the pixel values of the small blocks are obtained in total from the eight result images. The averaging unit 82 supplies the obtained average values to the vectorization unit 83.

The vectorization unit 83 generates a 128-dimensional vector that is a characteristic amount of the 128 average values supplied from the averaging unit 82 as a characteristic amount vector indicating the characteristic of the part image. When the characteristic amount vector is denoted with v, for example, the characteristic amount vector v is expressed as in equation (4) below.

$$v = (g1_{b1}, \ldots, g1_{b16}, g2_{b1}, \ldots, g2_{b16}, \ldots, g8_{b1}, \ldots, g8_{b16}) \quad (4)$$

In addition, $gi_{bj}$ indicates the average of the pixel values of $j^{th}$ small block of the $i^{th}$ result image.

The vectorization unit 83 supplies the generated characteristic amount vector to the learning unit 53.

In step S3, the learning unit 53 accumulates learning data. In particular, for example, the user inputs correct data indicating which one is captured among cheeks, a nose, a forehead, and a back of the hand as the part image to the learning unit 53. The learning unit 53 causes the storage unit 54 to store the learning data of which the acquired correct data and the characteristic amount vector are associated with each other.

In step S4, the learning unit 53 determines whether or not the learning data is sufficiently accumulated. When it is determined that the learning data is not yet sufficiently accumulated, the process returns to step S1.

In step S4, processes from step S1 to step S4 are then repeatedly carried out until it is determined that the learning data is sufficiently accumulated.

For example, the user captures a plurality of part images by shifting the location of the part of each of cheeks, a nose, a forehead, and a back of the hand of the subject little by little. The image processing system 1 then generates and accumulates the learning data in each of the captured part images. The process described above is performed on a plurality of subjects. The learning data in a plurality of locations of each part of each of the plurality of subjects is thus accumulated.

In step S4, when it is determined that the learning data is sufficiently accumulated, the process proceeds to step S5.

In step S5, the learning unit 53 generates a discriminator.

For example, the learning unit 53 generates a discriminator using a support vector machine (SVM) based on the learning data accumulated in the storage unit 54 as identification information used to identify the part within the part image on the basis of the characteristic amount vector extracted from the part image. The learning unit 53 then causes the generated discriminator to be stored in the storage unit 54.

The learning process is then finished.

Skin Measurement and Analysis Process

Figure 7:
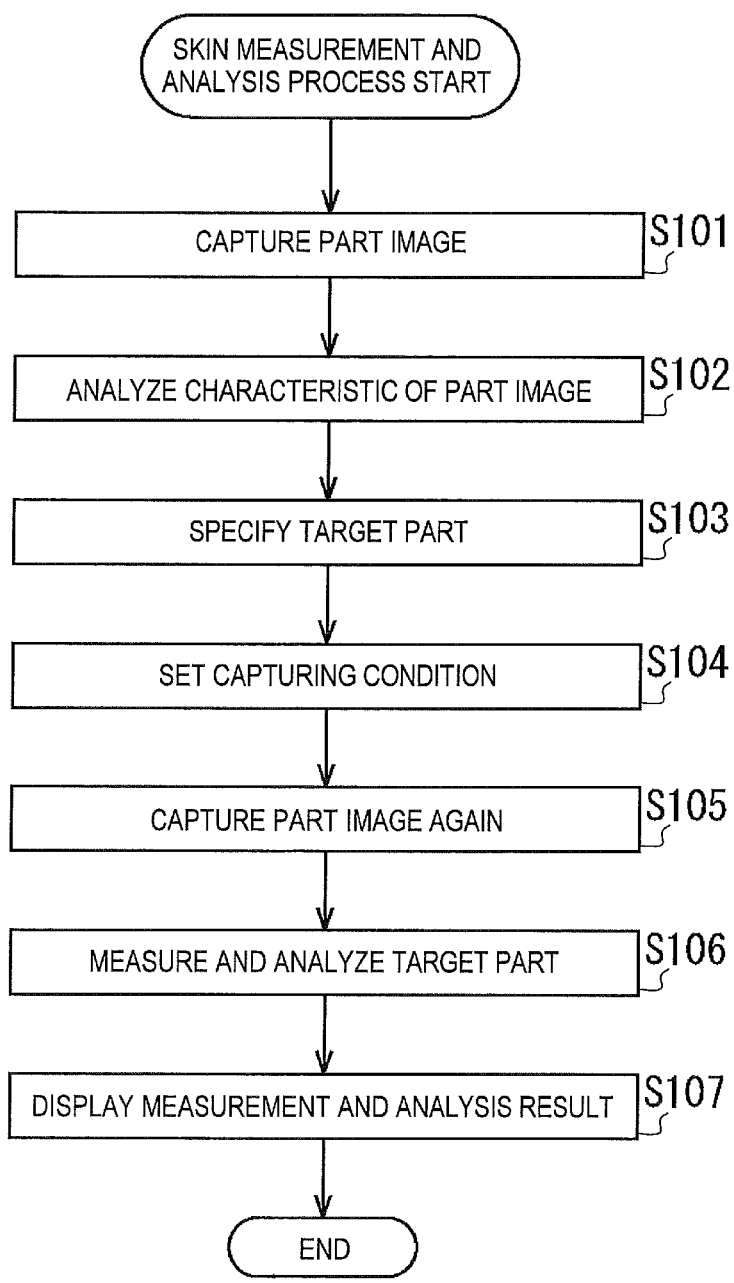
FIG. 7 is a flowchart illustrating a skin measurement analysis process.

Next, the skin measurement and analysis process carried out by the image processing system 1 will be described with reference to the flowchart of FIG. 7.

In addition, for example, this process is initiated when an instruction to initiate the skin measurement and analysis process is input to the image processing system 1 through an input unit not shown.

Figure 5:
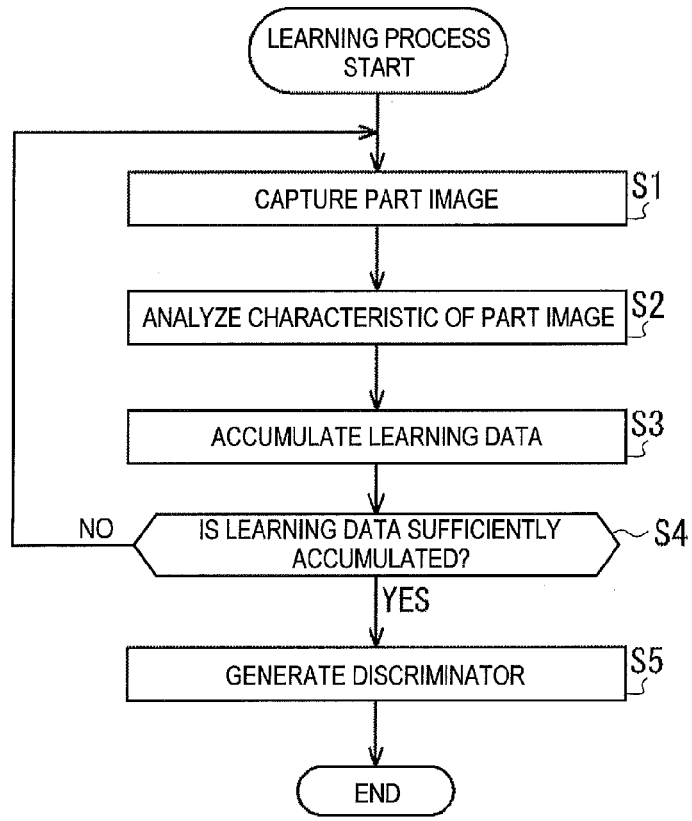
FIG. 5 is a flowchart illustrating a learning process.

In step S101, the part image of the part as the target where the skin state of the subject is measured is captured in the same manner as in the process of step S1 of FIG. 5.

In step S102, the characteristic of the part image is analyzed in the same manner as in the process of step S2 of FIG. 5. The characteristic amount vector obtained from the process is then supplied from the characteristic analysis unit 52 to the part specifying unit 55.

In step S103, the part specifying unit 55 specifics the target part. In particular, the part specifying unit 55 specifies the part of the subject (target part) reflected in the part image from cheeks, a nose, a forehead, and a back of the hand on the basis of the characteristic amount vector extracted by the characteristic analysis unit 52 and the discriminator stored in the storage unit 54. The part specifying unit 55 notifies the capturing condition setting unit 56 and the skin measurement and analysis unit 57 of the specified target part.

In step S104, the image processing system 1 sets the capturing condition. In particular, the capturing condition setting unit 56 sets the capturing condition of the capturing device 11 on the basis of the target part specified by the part specifying unit 55 and the measurement condition setting table stored in the storage unit 54.

FIG. 8 illustrates an example of the measurement condition setting table. For example, the measurement condition setting table includes six items such as target part, wavelength, measurement depth, polarization direction, capturing range, and measurement item. Among these items, the wavelength, the measurement depth, the polarization direction, and the capturing range are items for setting the capturing condition of the capturing device 11, and values of each of the items are determined by at least one of the target part and the measurement items.

The wavelength indicates the wavelength of light used to capture the part image, and is set to a value suitable for capturing elements (e.g., skin ridge, keratin plug, and so forth) necessary to measure the measurement item of the target part, for example. In this example, two kinds of set values such as white light and UV light (wavelength 390 nm) are illustrated.

The measurement depth indicates how deep the measurement is performed from the skin surface. In this example, the depth is set to 0 mm (skin surface) for all cases.

The polarization direction indicates a relationship between the polarization direction of illumination light emitted from the illumination unit 32 and the polarization direction of incident light incident on the image sensor of the capturing unit 31. In this example, three kinds of set values such as parallel, orthogonal, and – (no polarization) are illustrated.

Here, parallel indicates that the polarization direction of the illumination light is made to be parallel to the polarization direction of the incident light, in other words, the polarization direction of the illumination light is made to be equal to the polarization direction of the incident light. It is thus possible to extract and capture light reflected from the surface of the target part by causing the polarization direction of the illumination light to be parallel to the polarization direction of the incident light.

Orthogonal indicates that the polarization direction of the illumination light is made to be orthogonal to the polarization direction of the incident light. It is thus possible to block out light reflected from the surface of the target part by causing the polarization direction of the illumination light to be orthogonal to the polarization direction of the incident light, and is thus possible to extract light having components (e.g., components reflected inside the skin) other than the reflected light.

(No polarization) indicates that there is no polarization between the illumination light and the incident light. The polarization direction is thus set on the basis of on which one measurement is performed between the surface and the inside of the target part, for example.

The capturing range indicates the range in which the part image is captured, and, for example, is set to an area that enables elements necessary to measure the measurement items of the target part to be captured. In this case, three kinds of set values such as 1 cm×1 cm, 3 cm×3 cm, and 5 cm×5 cm are illustrated.

For example, the measurement item is the texture when the target part is cheeks, however, the number of skin ridges or the like is measured as the texture state as will be described below. Since the size of the skin ridge is about 0.1 to 0.5 mm, the capturing range is set to 1 cm×1 cm, for example. In addition, the measurement item is the wrinkle when the target part is the forehead, however, since the length of the wrinkle of the forehead is about several cm, the capturing range is set to 5 cm×5 cm, for example.

The measurement item indicates the item to be measured on the target part. In this case, four kinds of set values such as texture, a keratin plug, a spot, and a wrinkle are illustrated.

The capturing condition setting unit 56 sets the capturing condition on the basis of wavelength, measurement depth, polarization direction, and capturing range with respect to the specified target part. For example, the capturing condition setting unit 56 sets the kind of the light source or the filter to be applied to capturing on the basis of the wavelength corresponding to the target part. In addition, for example, the capturing condition setting unit 56 sets the depth of the focus location of the capturing unit 31 from a surface of the target part on the basis of the measurement depth corresponding to the specified target part. In addition, for example, the capturing condition setting unit 56 sets the polarization direction of the capturing unit 31 and the polarization direction of the illumination unit 32 on the basis of the polarization direction corresponding to the specified target part. In addition, the capturing condition setting unit 56 sets capturing magnification of the capturing unit 31 on the basis of the capturing range corresponding to the specified target part.

The capturing condition setting unit 56 transmits capturing condition setting information indicating the set capturing conditions to the capturing device 11 through the communication unit 51. The control unit 35 of the capturing device 11 then receives the capturing condition setting information through the communication unit 34. The control unit 35 then performs setting on the capturing unit 31 and the illumination unit 32 on the basis of the received capturing condition setting information.

For example, the control unit 35 sets the kind of the light source or the filter to be employed and sets the wavelength of light used to capture the part image on the basis of the capturing condition setting information.

Here, a specific example of a method of setting the wavelength of light used to capture the part image will be described with reference to FIGS. 9 to 12. In addition, hereinafter, an example of setting the wavelength of light used to capture the part image from four kinds will be described.

Figure 9:
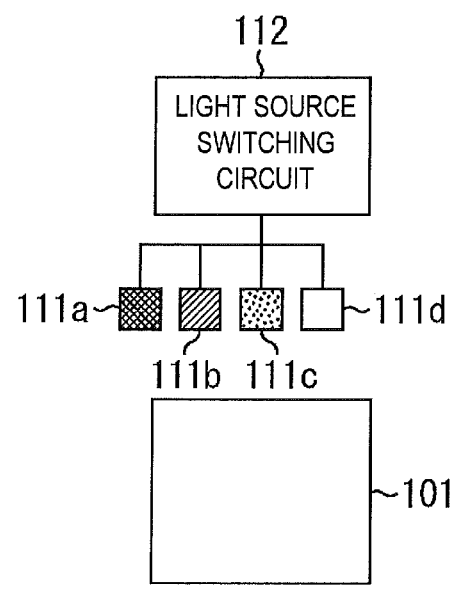
FIG. 9 is a diagram illustrating a first method of setting a wavelength of light used to capture a part image.

For example, as shown in FIG. 9, light sources 111a to 111d having different wavelengths from each other and a light source switching circuit 112 may be disposed in the illumination unit 32, and the light source to be used may be switched. The wavelength of the illumination light irradiated on the subject and the incident light incident on the image sensor 101 of the capturing unit 31 is thus switched. In addition, for example, the light sources 111a to 111d include light emitting diodes (LEDs).

Figure 10:
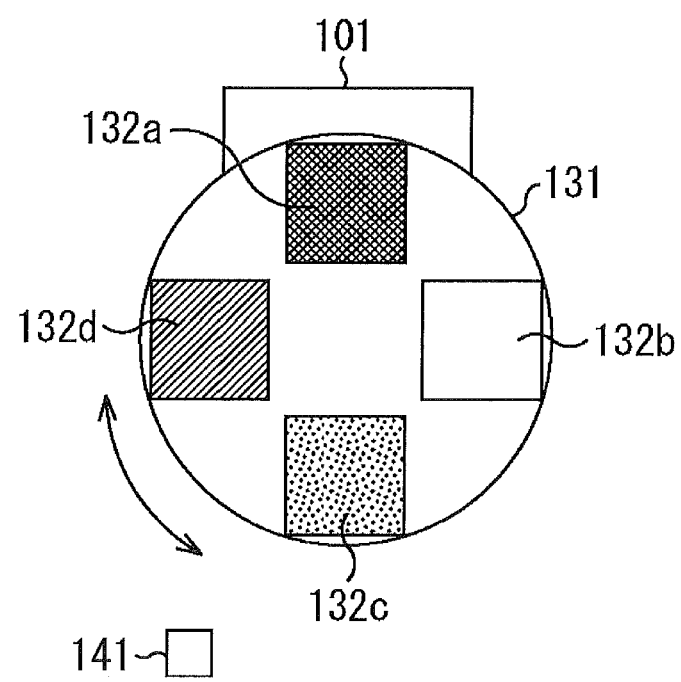
FIG. 10 is a diagram illustrating a second method of setting a wavelength of light used to capture a part image.

In addition, for example, as shown in FIG. 10, a turret 131 including band pass filters (BPFs) 132a to 132d having different transmission wavelength ranges from each other may be disposed in front of the image sensor 101, and a light source 141 emitting light in a wavelength band ranging from visible light to UV light may be disposed in the illumination unit 32. The wavelength of the incident light incident on the image sensor 101 may be switched by rotating the turret 131 and thus adjusting the location of the BPFs 132a to 132d. In addition, for example, the light source 141 includes an LED.

Figure 11:
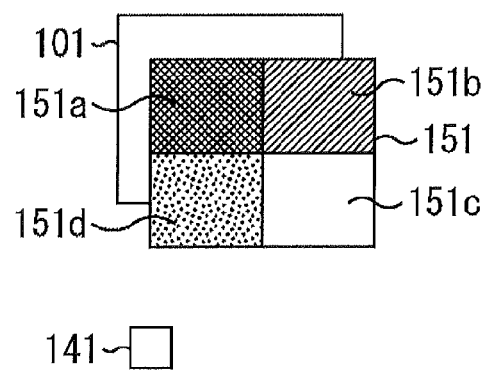
FIG. 11 is a diagram illustrating a third method of setting a wavelength of light used to capture a part image.

In addition, for example, as shown in FIG. 11, a four-way dividing filter 151 including BPFs 151a to 151d having different transmission wavelengths from each other may be disposed such that transmitting light of each BPF is incident on a different region of the image sensor 101, and the region of the image sensor 101 used to capture the part image may thus be switched.

Figure 12:
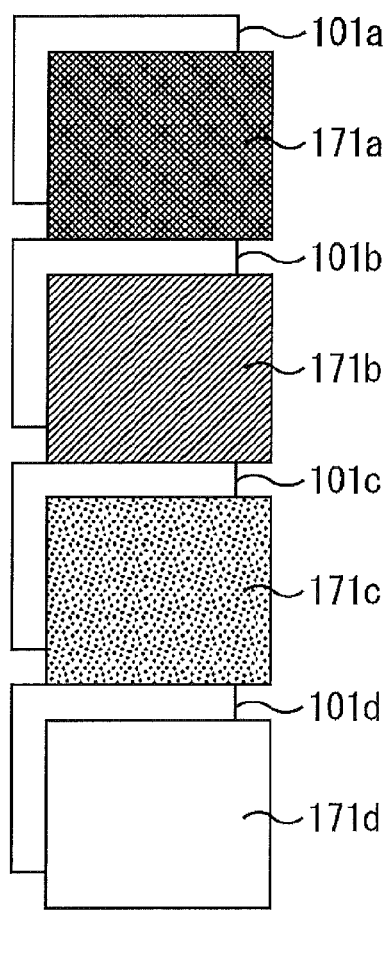
FIG. 12 is a diagram illustrating a fourth method of setting a wavelength of light used to capture a part image.
Figure 13:
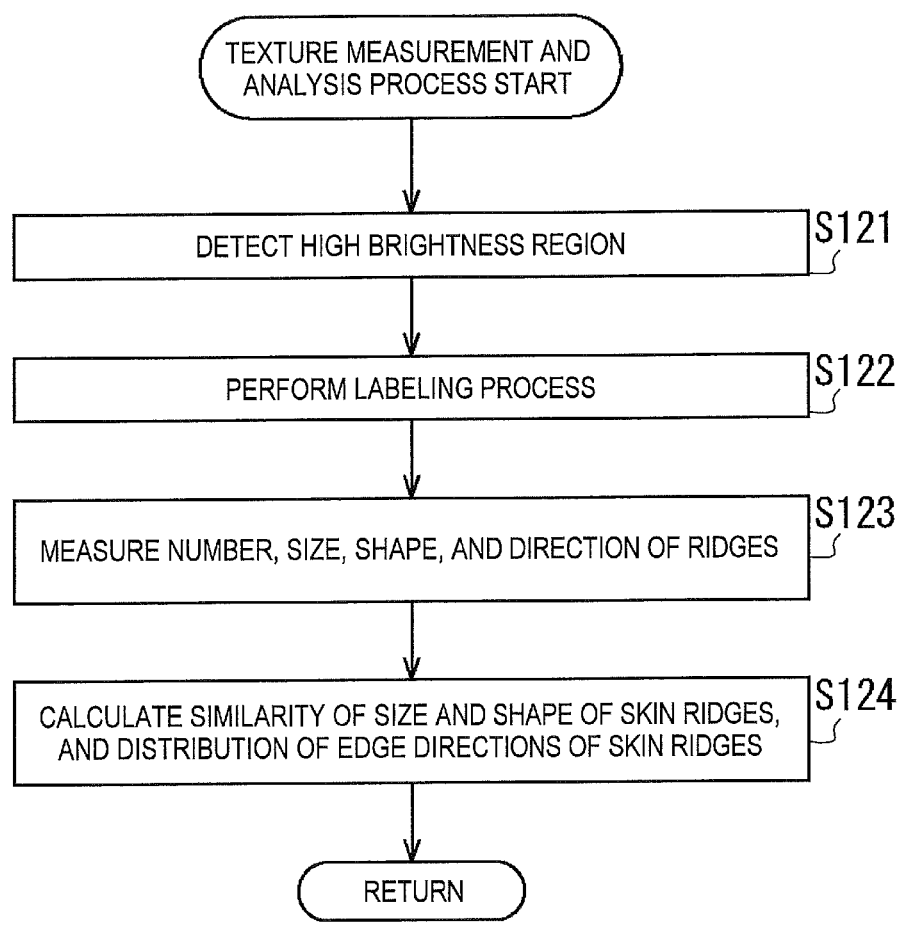
FIG. 13 is a flowchart illustrating a texture measurement analysis process.
Figure 14:
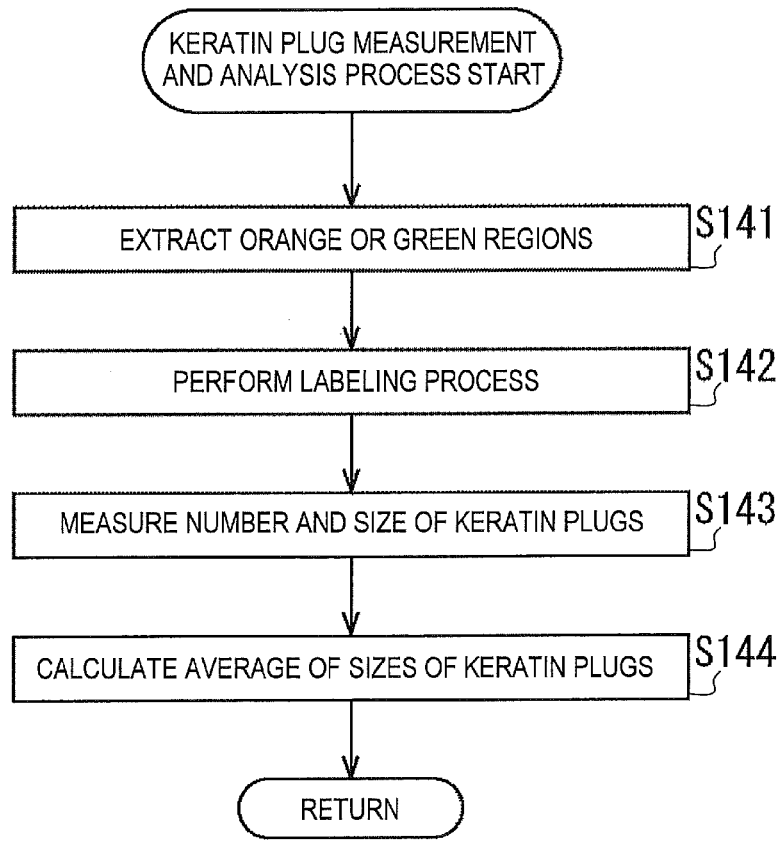
FIG. 14 is a flowchart illustrating a keratin plug measurement analysis process.

In addition, for example, as shown in FIG. 12, BPFs 171a to 171d having different transmission wavelength ranges from each other may be disposed so as to correspond to four image sensors 101a to 101d, and the image sensor used for capturing may thus be switched.

In addition, the control unit 35 sets the focus location of the capturing unit 31 on the basis of the capturing condition setting information. In this case, since the measurement depth of all target parts is 0 mm, the focus location is set to surfaces of all of the target parts regardless of the individual target parts.

In addition, the control unit 35 sets the polarization direction of illumination light emitted from the illumination unit 32 and the polarization direction of incident light incident on the image sensor of the capturing unit 31 on the basis of the capturing condition setting information.

In addition, the control unit 35 sets the capturing magnification of the zoom lens of the capturing unit 31 on the basis of the capturing condition setting information.

Referring back to FIG. 7, in step S105, the image processing system 1 performs the same process as in step S1 of FIG. 5, and captures the part image again under the capturing condition set in response to the target part. The captured part image is transmitted from the capturing device 11 to the image processing device 12 and then supplied to the skin measurement and analysis unit 57.

In step S106, the skin measurement and analysis unit 57 performs measurement and analysis on the target part. In particular, the skin measurement and analysis unit 57 specifies items to be measured and analyzed on the target part on the basis of the target part specified by the part specifying unit 55 and the measurement condition setting table stored in the storage unit 54.

When the target part is the cheeks, the texture measurement and analysis unit 71 of the skin measurement and analysis unit 57 measures the texture state of the cheeks and analyzes the measurement result. Here, details of the texture measurement and analysis process carried out by the texture measurement and analysis unit 71 will be described with reference to the flowchart of FIG. 13.

In step S121, the texture measurement and analysis unit 71 detects a high brightness region. In particular, the skin ridge regions tend to be brighter than other regions such as skin grooves in the part image. For example, the texture measurement and analysis unit 71 thus binarizes the part image using a predetermined threshold value and extracts the high brightness regions from the binarized image.

In step S122, the texture measurement and analysis unit 71 performs a labeling process. As a result, the extracted high brightness regions are individually identified.

In step S123, the texture measurement and analysis unit 71 measures the number, size, shape, and direction of the skin ridges. In particular, the texture measurement and analysis unit 71 obtains the number of skin ridges within the part image by counting the number of identified high brightness regions. In addition, the texture measurement and analysis unit 71 measures the shape and size of each high brightness region as the shape and size of the skin ridge. In addition, the texture measurement and analysis unit 71 measures a direction of an edge portion of each high brightness region.

In step S124, the texture measurement and analysis unit 71 calculates the similarity of the size and shape of the skin ridges and the distribution of edge directions of the skin ridges.

For example, fineness of the texture of the target part is evaluated by the number of skin ridges. In addition, for example, uniformity of the texture of the target part is evaluated by the similarity of size and shape of the skin ridges and the distribution of edge directions of the skin ridges.

The texture measurement and analysis process is then finished.

In addition, when the target part is the nose, the keratin plug measurement and analysis unit 72 of the skin measurement and analysis unit 57 measures the state of the keratin plug of the nose and analyzes the measurement result. Here, details of the keratin plug measurement and analysis process carried out by the keratin plug measurement and analysis unit 72 will be described with reference to the flowchart of FIG. 14.

In step S141, the keratin plug measurement and analysis unit 72 extracts orange or green regions.

Figure 15:
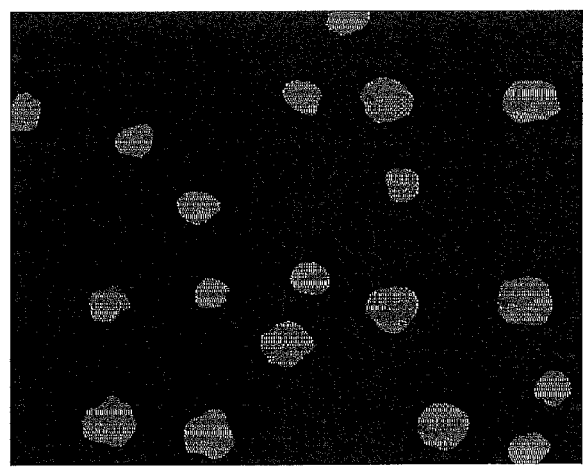
FIG. 15 is a diagram schematically illustrating a part image in which a surface of a nose is captured using ultraviolet (UV) light.
Figure 16:
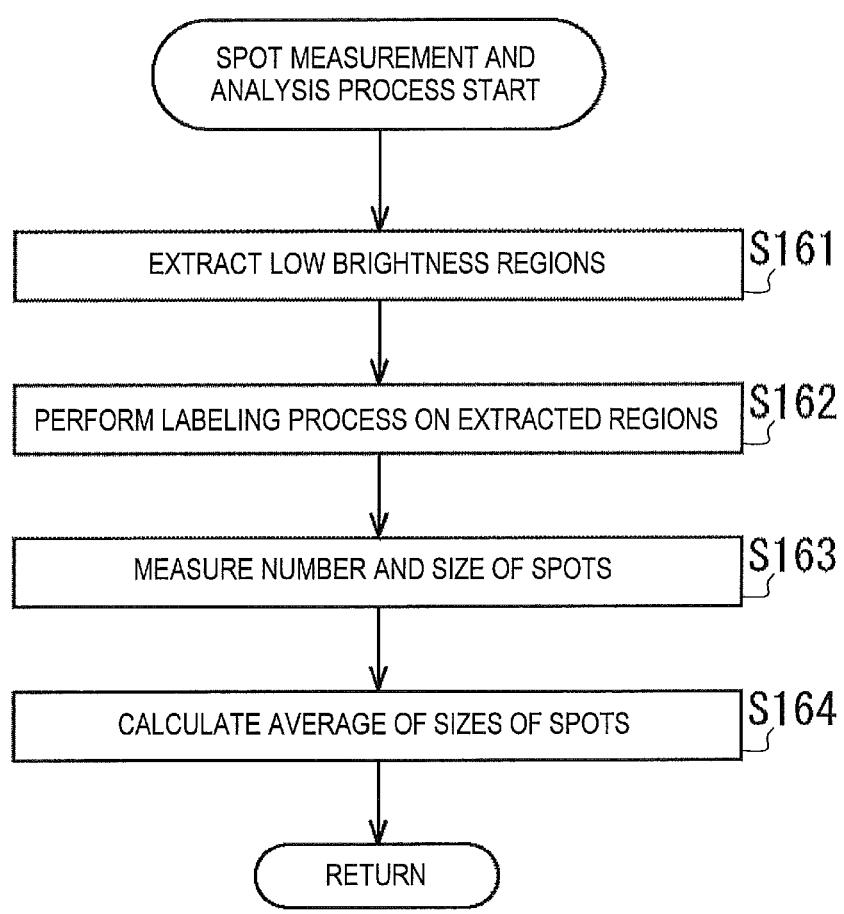
FIG. 16 is a flowchart illustrating a spot measurement analysis process.
Figure 17:
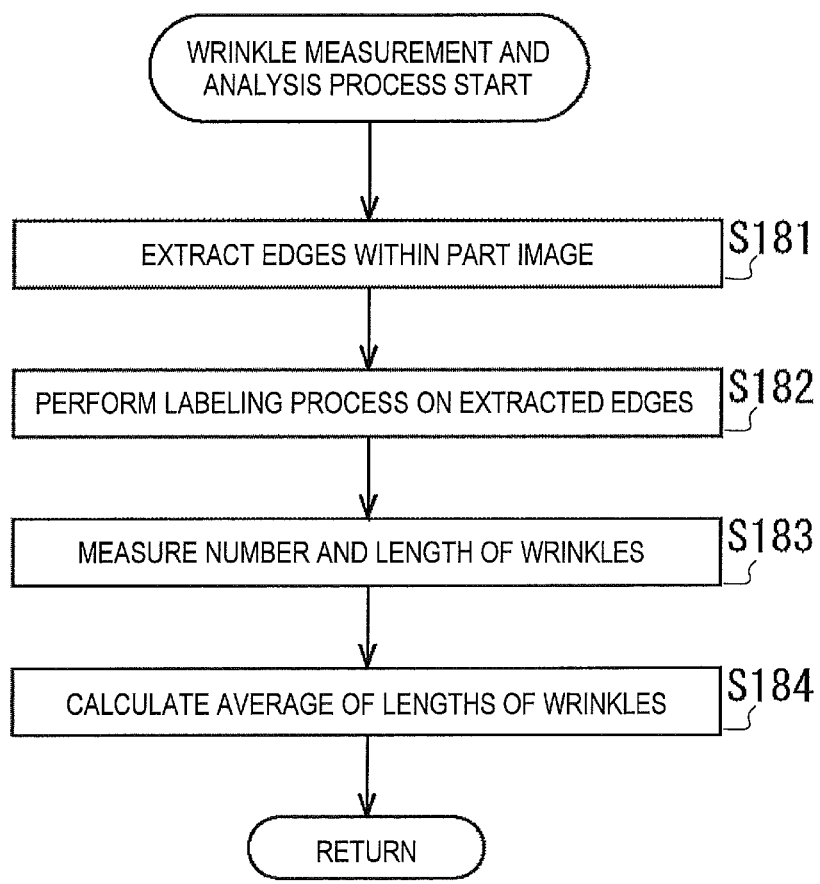
FIG. 17 is a flowchart illustrating a wrinkle measurement analysis process.

FIG. 15 schematically illustrates the part image of which a surface of the nose is captured using UV light. In addition, portions illustrated in gray in FIG. 15 are regions of the keratin plugs.

When the surface of the nose is captured using the UV light, regions of the keratin plugs illustrated in gray in FIG. 15 exhibit colors close to orange or green, and stand out against the others. In addition, one color such as gray is illustrated in FIG. 15, however, color or brightness actually changes within the region.

The keratin plug measurement and analysis unit 72 thus extracts the orange or green regions as regions at which the keratin plugs within the part image are reflected.

In step S142, the keratin plug measurement and analysis unit 72 performs the labeling process. As a result, the extracted orange or green regions are individually identified.

In step S143, the keratin plug measurement and analysis unit 72 measures the number and size of the keratin plugs. In particular, the keratin plug measurement and analysis unit 72 obtains the number of keratin plugs within the part image by counting the number of identified orange or green regions. In addition, the keratin plug measurement and analysis unit 72 measures the size of each of the orange or green regions as the size of the keratin plug.

In step S144, the keratin plug measurement and analysis unit 72 calculates an average of the sizes of the keratin plugs.

For example, an amount of the keratin plugs of the target part is evaluated by the number of keratin plugs and the average of the sizes of the keratin plugs.

The keratin plug measurement and analysis process is then finished.

In addition, when the target part is the back of the hand, the spot measurement and analysis unit 73 of the skin measurement and analysis unit 57 measures the spot of the back of the hand and analyzes the measurement result. Here, details of the spot measurement and analysis process carried out by the spot measurement and analysis unit 73 will be described with reference to the flowchart of FIG. 16.

In step S161, the spot measurement and analysis unit 73 extracts low brightness regions. In particular, spot regions appear as blackish regions in the part image. The spot measurement and analysis unit 73 thus binarizes the part image, for example, using a predetermined threshold value, and extracts the low brightness regions from the binarized image.

In step S162, the spot measurement and analysis unit 73 performs the labeling process. As a result, the extracted low brightness regions are individually identified.

In step S163, the spot measurement and analysis unit 73 measures the number and sizes of the spots. In particular, the spot measurement and analysis unit 73 obtains the number of spots within the part image by counting the number of identified low brightness regions. In addition, the spot measurement and analysis unit 73 measures the size of each low brightness region as the size of the spot.

In step S164, the spot measurement and analysis unit 73 calculates an average of the sizes of the spot regions.

An amount of the spots of the target part is thus evaluated by the number of spots and the average of the sizes, for example.

The spot measurement and analysis process is then finished.

In addition, when the target part is the forehead, the wrinkle measurement and analysis unit 74 of the skin measurement and analysis unit 57 measures the wrinkle of the forehead and analyzes the measurement result. Here, details of the wrinkle measurement and analysis process carried out by the wrinkle measurement and analysis unit 74 will be described with reference to the flowchart of FIG. 17.

Figure 18:
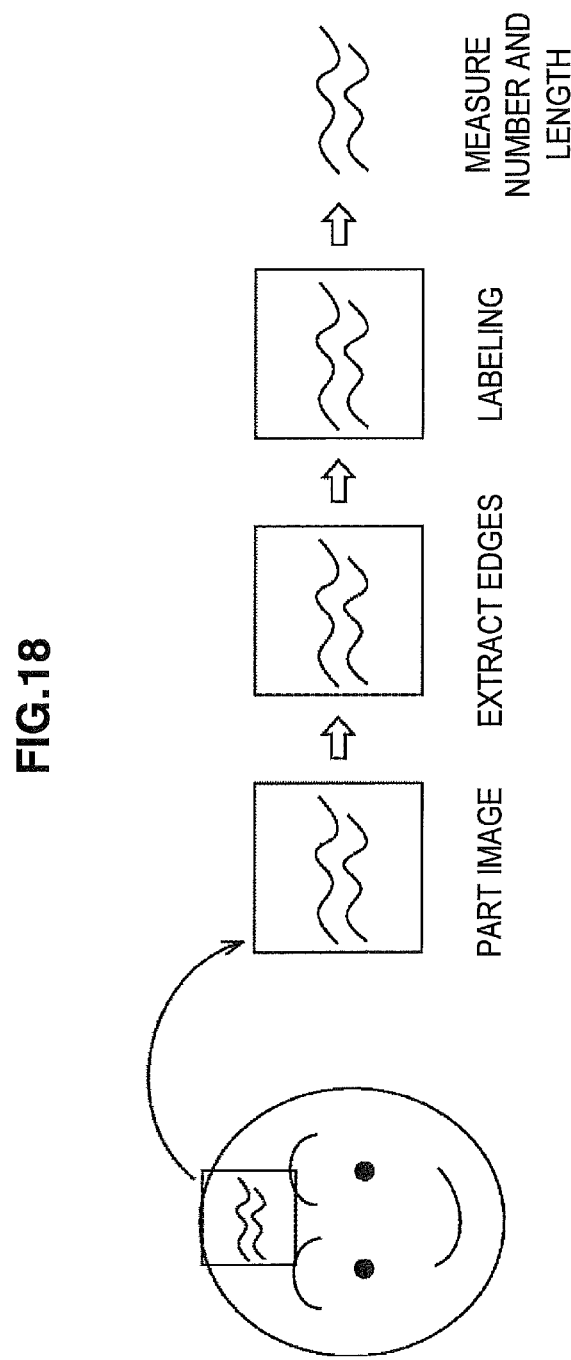
FIG. 18 is a diagram illustrating a flow of a wrinkle measurement analysis process.

In step S181, the wrinkle measurement and analysis unit 74 extracts edges within the part image. That is, the wrinkle measurement and analysis unit 74 extracts edge regions within the part image using a Sobel filter or the like so as to extract the wrinkle reflected in the part image as shown in FIG. 18.

In step S182, the wrinkle measurement and analysis unit 74 performs a labeling process. As a result, each of the extracted edge regions is individually identified.

In step S183, the wrinkle measurement and analysis unit 74 measures the number and the sizes of the wrinkles. In particular, the wrinkle measurement and analysis unit 74 obtains the number of wrinkles within the part image by counting the number of identified edge regions. In addition, the wrinkle measurement and analysis unit 74 measures the length of each wrinkle within the part image by counting connection pixels of each edge region.

In step S184, the wrinkle measurement and analysis unit 74 calculates an average of the lengths of the wrinkles.

An amount of the wrinkles of the target part is thus evaluated by the number of wrinkles and the average of the lengths of the wrinkles, for example.

The wrinkle measurement and analysis process is then finished.

Referring back to FIG. 7, in step S107, the image processing system 1 displays the measurement and analysis result.

In particular, the skin measurement and analysis unit 57 supplies the part image and the measurement and analysis result of the target part to the display control unit 58. The display control unit 58 generates data indicating the measurement and analysis result of the skin state of the target part on the basis of the part image and the measurement and analysis result of the target part, and transmits the data to the display device 13 through the communication unit 51. The display device 13, for example, displays the measurement and analysis result of the skin state of the target part along with the part image on the basis of the received data.

The skin measurement and analysis process is then finished.

As described above, it is possible to automatically specify the target part, capture the part image under the condition suitable for the target part, and perform measurement and analysis on items according to the target part. The user can thus correctly and simply measure and analyze the skin state of a desired part without fail.

In addition, it is possible to simply increase the kind of the target part by increasing the part on which the learning process is performed.

In addition, it is possible to simply change the measurement item or the capturing condition by changing the measurement condition setting table.

Modified Example of Measurement Condition Setting Table

Here, a case of using the measurement condition setting table of FIG. 19 instead of the measurement condition setting table of FIG. 8 will be described.

The capturing condition and the measurement item of the measurement condition setting table of FIG. 19 is different from the measurement condition setting table of FIG. 8. In particular, as the capturing condition of the cheeks, the wavelength is set to UV light, the measurement depth is set to 0.2 mm, and the polarization direction is set to an orthogonal direction in the measurement condition setting table of FIG. 19. Accordingly, when the target part is the cheeks, the part image of the cheeks is captured under the set condition.

In addition, the measurement depth of the cheeks is different from the measurement depth of other parts. This difference will be described with reference to FIG. 20.

Figure 20:
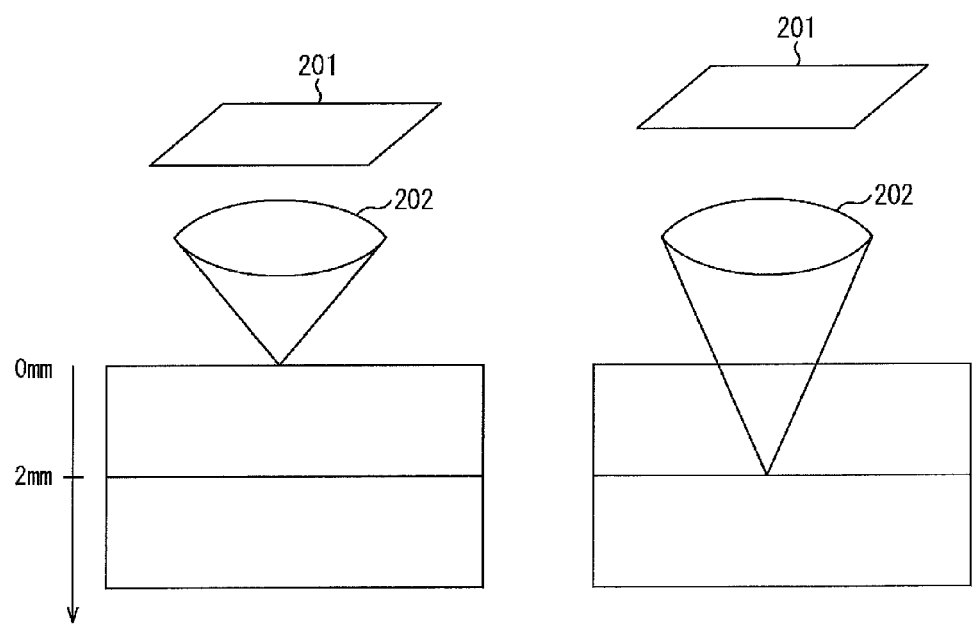
FIG. 20 is a diagram illustrating an example of a focus setting location of a capturing device with respect to a measurement depth.

FIG. 20 is a diagram schematically illustrating states of the image sensor 201 and the lens 202 of the capturing unit 31 of the capturing device 11.

Since the measurement depth is 0.0 mm when the target part is a part other than the cheeks, the focus location of the lens 202 is set to a surface of the target part as shown in the left side of FIG. 20.

On the other hand, since the measurement depth is 0.2 mm when the target part is the cheeks, the focus location of the lens 202 is set to a location 0.2 mm deep from the surface of the target part as shown in the right side of FIG. 20. Since an average thickness of the human epidermis is about 0.2 mm, it is possible to detect spots that are slightly inside the surface of the cheeks and will appear on the surface in the future.

2. Modifications

Hereinafter, modified examples of the embodiments of the present technology will be described.

Modification 1

Although the image processing system 1 including the capturing device 11, the image processing device 12, and the display device 13 has been described, the present technology may be embodied by other configurations.

For example, the capturing device 11, the image processing device 12, and the display device 13 may be integrated to be one device. In addition, for example, two of the capturing device 11, the image processing device 12, and the display device 13 may be integrated.

In addition, disposition of functions of the capturing device 11 and the image processing device 12 are not limited to the examples described above, for example, some of the functions of the capturing device 11 may be disposed in the image processing device 12 and some of the functions of the image processing device 12 may be disposed in the capturing device 11.

In addition, the display device 13 may be disposed to be dedicated to the image processing system 1, and display devices of other devices such as a television receiver or a cellular phone may also be employed.

Figure 21:
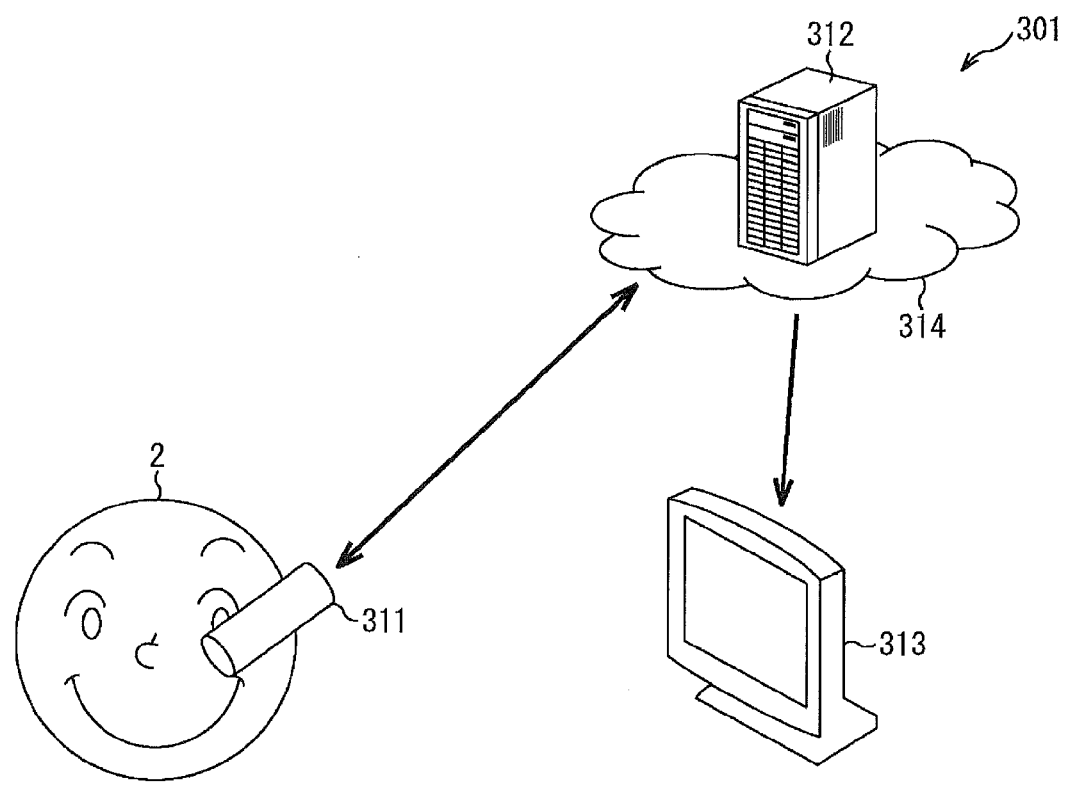
FIG. 21 is a diagram illustrating a second embodiment of an image processing system to which the present technology is applied.

In addition, for example, the present technology may be embodied by the system that performs a remote process through the network such as the image processing system 301 of FIG. 21.

The image processing system 301 includes a capturing device 311, a server 312, and a display device 313. The capturing device 311, the server 312, and the display device 313 correspond to the capturing device 11, the image processing device 12, and the display device 13, and perform almost the same processes, respectively.

The capturing device 311, the server 312, and the display device 313 are connected to each other through the network 314 to perform communication. In addition, communication methods between the capturing device 311, the server 312, and the display device 313 are not limited to particular methods, but arbitrary wired or wireless communication methods may be employed.

Figure 22:
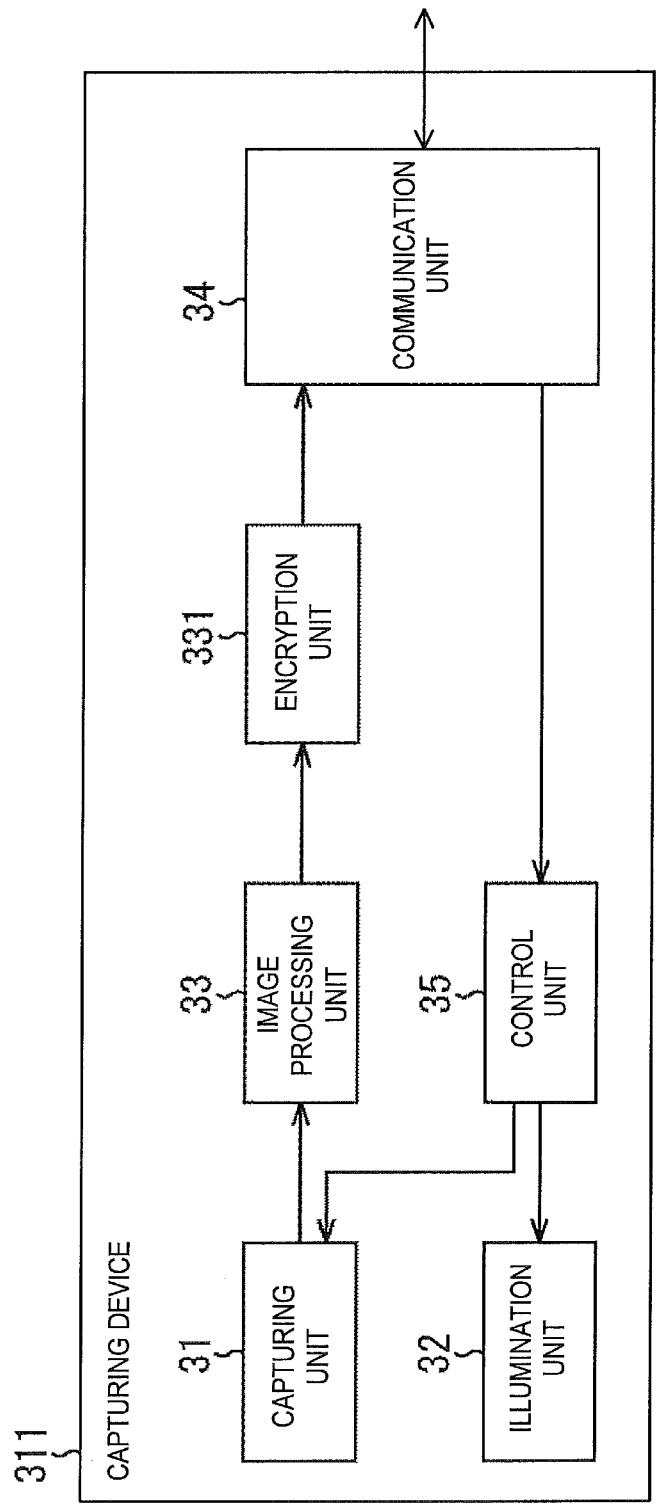
FIG. 22 is a diagram illustrating a configuration example of functions of a capturing device.

FIG. 22 is a block diagram illustrating a configuration example of the functions of the capturing device 311. In addition, portions of FIG. 22 corresponding to those of FIG. 2 are denoted with the same numerals, and the description of the portions at which the same processes are carried out will not be repeated, but rather, omitted.

The capturing device 311 differs from the capturing device 11 of FIG. 2 in that an encryption unit 331 is disposed between the image processing unit 33 and the communication unit 34.

The encryption unit 331 encrypts or scrambles the part image captured by the capturing unit 31 using a predetermined method so as to ensure security in a transmission path between the capturing device 311 and the server 312. The encryption unit 331 supplies the encrypted or scrambled part image to the communication unit 34.

Figure 23:
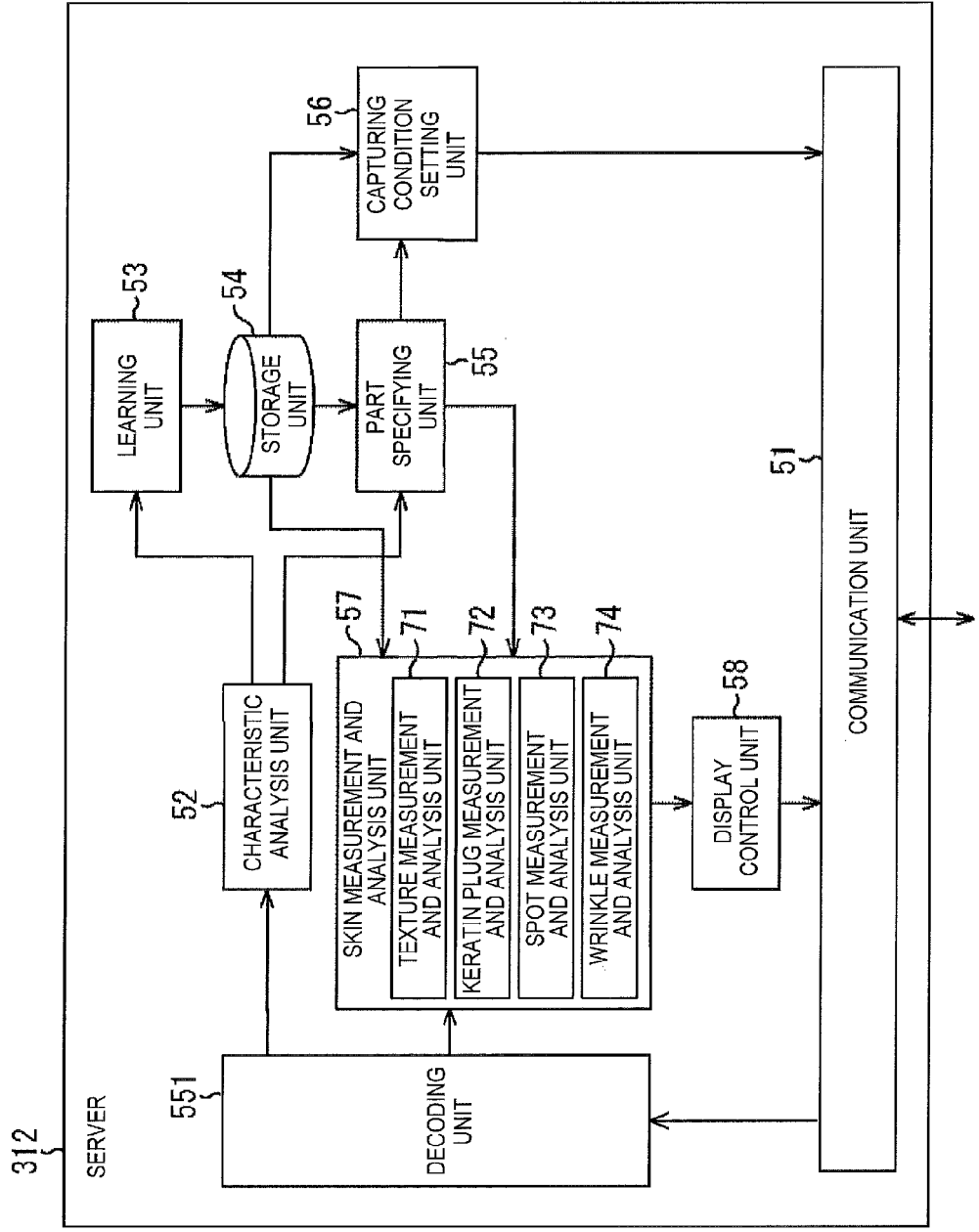
FIG. 23 is a block diagram illustrating a configuration example of functions of a server.

FIG. 23 is a block diagram illustrating a configuration example of the functions of the server 312. In addition, portions of FIG. 23 corresponding to those of FIG. 3 are denoted with the same numerals, and the description of the portions where the same processes are carried out will not be repeated, but rather, omitted.

The server 312 differs from the image processing device 12 of FIG. 3 in that a decoding unit 551 is disposed between the communication unit 51, the characteristic analysis unit 52, and the skin measurement and analysis unit 57.

The decoding unit 551 receives the part image from the capturing device 311 through the network 314 and the communication unit 51. The decoding unit 551 decodes the encrypted or scrambled part image, and supplies the decoded part image to the characteristic analysis unit 52 or the skin measurement and analysis unit 57.

Modification 2

Methods of analyzing the characteristic of the part image of the characteristic analysis unit 52 are not limited to those described above, but other methods, for example, those of extracting color information or the like as the characteristic amount using other edge extraction filters, may be employed.

Modification 3

Learning methods of the learning unit 53 are not limited to the SVM mentioned above, but other learning methods, for example, linear discriminant analysis, neural net, and so forth, may be employed.

In addition, the learning unit 53 may not be disposed in the image processing device 12, and the result of another device carrying out the learning process may be given to the image processing device 12.

Modification 4

The target parts and the measurement items described above are merely examples, and arbitrary target parts and measurement items may be added or deleted. In addition, combinations of the target part and the measurement items may be set to be different from the examples described above, or a plurality of measurement items may be set for one target part.

Modification 5

The capturing conditions are merely examples, and arbitrary conditions may be added or deleted. For example, intensity of illumination light, exposure of the capturing unit 31, capturing angle, and so forth may be set.

Modification 6

The present technology may also be applied to a case of measuring and analyzing the skin state of a living body other than a human being.

In addition, for example, the present technology may also be applied to cases not of analyzing the measurement result but only of measuring the skin state, displaying the measurement result only, recording the measurement result only, or supplying the measurement result to other devices.

In addition, for example, the present technology may also be applied to a case of not performing measurement and analysis on the skin state. For example, the present technology may also be applied to a case of displaying and recording the part image captured under the capturing condition in response to the specified part, or supplying the part image to other devices.

Configuration Example of Computer

The series of processes described above may be carried out by software or hardware. When the series of processes are carried out by the software, a program constituting the software is installed in a computer. Here, the computer includes, for example, a computer built in dedicated hardware, and a computer in which various programs are installed and various functions are carried out such as a general purpose personal computer.

Figure 24:
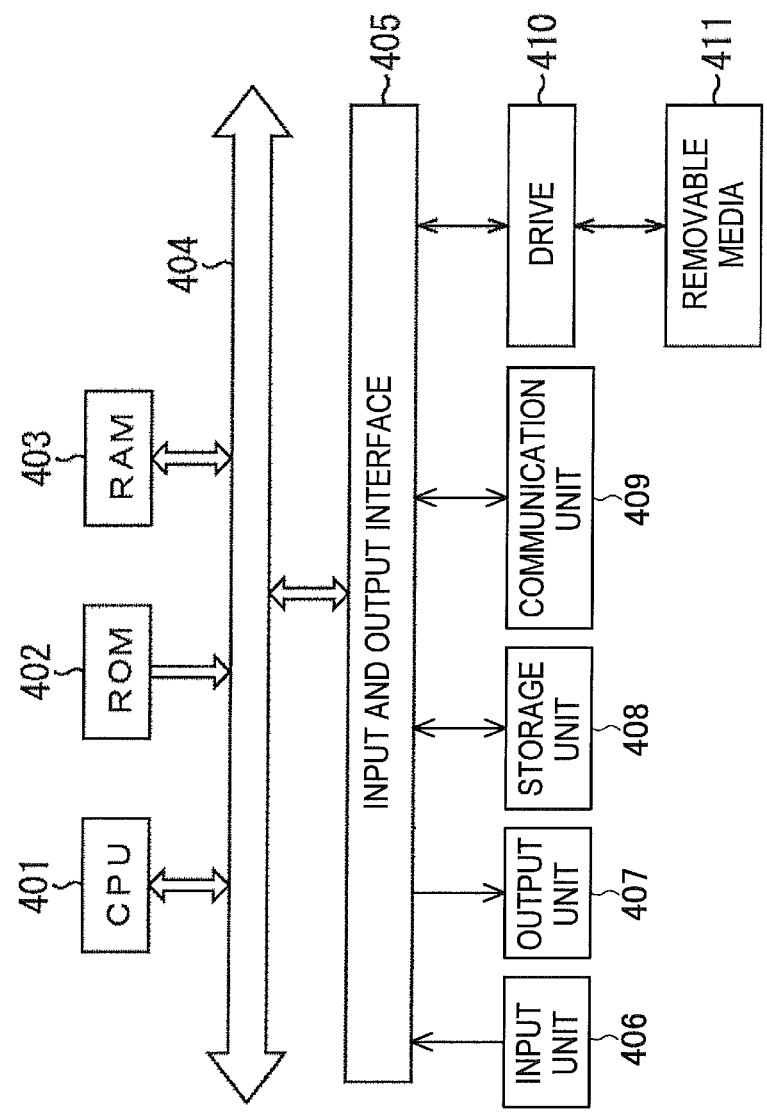
FIG. 24 is a block diagram illustrating a configuration example of a computer.

FIG. 24 is a block diagram illustrating a configuration example of the computer hardware carried out by the series of processes described above.

A central processing unit (CPU) 401, a read only memory (ROM) 402, and a random access memory (RAM) 403 are connected to each other by a bus 404 in the computer.

In addition, an input and output interface 405 is connected to the bus 404. An input unit 406, an output unit 407, a storage unit 408, a communication unit 409, and a drive 410 are connected to the input and output interface 405.

The input unit 406 includes a keyboard, a mouse, a microphone, and so forth. The output unit 407 includes a display, a speaker, and so forth. The storage unit 408 includes a hard disk, a non-volatile memory, and so forth. The communication unit 409 includes a network interface, and so forth. The drive 410 drives removable media 411 such as a magnetic disk, an optical disc, a magneto-optical disc, and a semiconductor memory.

In the computer described above, for example, the series of processes are carried out by the CPU 401 that causes the program stored in the storage unit 408 to be loaded onto the RAM 403 through the input and output interface 405 and the bus 404 and then executed.

The program carried out by the computer (CPU 401), for example, may be recorded on the removable media 411 as package media and provided. In addition, the program may be provided through wired or wireless transmission media such as a local area network, the Internet, and digital satellite broadcasting.

In the computer, the program may be installed in the storage unit 408 through the input and output interface 405 by mounting the removable media 411 on the drive 410. In addition, the program may be received at the communication unit 409 through the wired or wireless transmission medium and then installed on the storage unit 408. Also, the program may be installed on the ROM 402 or the storage unit 408 in advance.

In addition, the program carried out by the computer may be a program of which the processes are carried out in time series in accordance with the order described in the present specification, or may be a program of which the processes are carried out in parallel or at a required timing when called upon.

In addition, the term system means a general device configured to include a plurality of devices, means, and so forth in the present specification.

In addition, the embodiments of the present technology are not limited to the embodiments described above, but may be variously changed within the scope without departing from the subject matter of the present technology.

In addition, for example, the present technology may include the configurations below.

(1) An image processing device including:
a specifying unit configured to specify a part of a living body within a first image on the basis of a characteristic amount of the first image capturing skin of the living body; and
a setting unit configured to set a capturing condition under which a second image indicating a state of the skin of the part is captured in response to the specified part.

(2) The image processing device according to (1), further including:
a measurement unit configured to measure the state of the skin of the specified part on the basis of the second image captured under the set capturing condition.

(3) The image processing device according to (2), wherein the measurement unit measures at least one of texture, a wrinkle, a spot, and a keratin plug of the skin in the specified part.

(4) The image processing device according to (2), further including:
a display control unit configured to control display of a measurement result of the part.

(5) The image processing device according to any one of (1) to (4), wherein the setting unit sets at least one of a wavelength of light used to capture the second image, a depth of a focus location from a surface of the part, a relationship between a polarization direction of illumination light and a polarization direction of incident light incident on an image sensor, and a capturing magnification on the basis of at least one of the part and measurement items in the part.

(6) The image processing device according to any one of (1) to (5), further including:
a characteristic analysis unit configured to extract a characteristic amount of the first image,
wherein the specifying unit specifies the part of the living body within the first image on the basis of the characteristic amount extracted by the characteristic analysis unit.

(7) The image processing device according to (6), further including:
a learning unit configured to learn identification information for identifying the part of the living body on the basis of the characteristic amount,
wherein the specifying unit specifies the part of the living body within the first image on the basis of the characteristic amount extracted by the characteristic analysis unit and the identification information learned by the learning unit.

(8) The image processing device according to any one of (1) to (7), further including:
a capturing unit configured to capture the living body.

(9) An image processing method including:
by an image processing device,
specifying a part of a living body within a first image on the basis of a characteristic amount of the first image capturing skin of the living body; and
setting a capturing condition under which a second image indicating a state of the skin of the part is captured in response to the specified part.

(10) A program for causing a computer to execute processes including:
specifying a part of a living body within a first image on the basis of a characteristic amount of the first image capturing skin of the living body; and
setting a capturing condition under which a second image indicating a state of the skin of the part is captured in response to the specified part.

(11) A computer-readable recording medium having the program according to (10) recorded thereon.

(12) An image processing system including:
a capturing device; and
an image processing device,
wherein the image processing device includes
a specifying unit configured to specify a part of a living body within a first image on the basis of a characteristic amount of the first image of skin of the living body captured by the capturing device; and
a setting unit configured to set, on the capturing device, a capturing condition under which a second image indicating a state of the skin of the part is captured in response to the specified part.

What is claimed is:
1. An image processing device comprising:
a central processing unit (CPU) configured to execute a program, in which upon execution of the program the CPU is caused to operate as:
a characteristic analysis unit configured to extract a characteristic amount of a first image;
a learning unit configured to accumulate learning data, to determine when a predetermined amount of learning data has been accumulated, and when a determination result thereof indicates that the predetermined amount of learning data has been accumulated to generate a discriminator based on the accumulated learning data, said discriminator being identification information for identifying a part of a living body on the basis of the characteristic amount;
a specifying unit configured to specify the part of the living body within the first image on the basis of the characteristic amount of the first image capturing skin of the living body extracted by the characteristic analysis unit and the identification information learned by the learning unit; and
a setting unit configured to set a number of capturing conditions under which a second image indicating a state of the skin of the part is captured in response to the specified part,
in which one of the capturing conditions set by the setting unit is a depth of a focus location from a surface of the part based on a measurement depth value indicative of how deep a measurement is to be performed from a surface of the skin part and another one of the capturing conditions set by the setting unit is a set polarization direction which indicates a relationship between a polarization direction of illumination light and a polarization direction of incident light incident on an image sensor, in which the set polarization direction has a value selected from one of a parallel value, an orthogonal value, or a no value, and in which the parallel value indicates that the polarization direction of illumination light is parallel to the polarization direction of incident light, the orthogonal value indicates that the polarization direction of the illumination light is orthogonal to the polarization direction of incident light, and the no value indicates that there is no polarization between the illumination light and the incident light.

2. The image processing device according to claim 1, in which upon execution of the program the CPU is further caused to operate as:

a measurement unit configured to measure the state of the skin of the specified part on the basis of the second image captured under the set capturing conditions.

3. The image processing device according to claim 2, wherein the measurement unit measures at least one of texture, a wrinkle, a spot, and a keratin plug of the skin in the specified part.

4. The image processing device according to claim 2, further comprising:

a display control unit configured to control display of a measurement result of the part.

5. The image processing device according to claim 1, wherein the setting unit in addition to the depth and the set polarization direction sets at least one of a wavelength of light used to capture the second image and a capturing magnification on the basis of at least one of the part and measurement items in the part.

6. The image processing device according to claim 1, further comprising:

a capturing unit configured to capture the living body.

7. An image processing method comprising:

by an image processing device, extracting a characteristic amount of a first image;

accumulating learning data, determining when a predetermined amount of learning data has been accumulated, and when a determination result thereof indicates that the predetermined amount of learning data has been accumulated generating a discriminator based on the accumulated learning data, said discriminator being identification information for identifying a part of a living body on the basis of the characteristic amount;

specifying the part of the living body within the first image on the basis of the extracted characteristic amount of the first image capturing skin of the living body and the learned identification information; and setting a number of capturing conditions under which a second image indicating a state of the skin of the part is captured in response to the specified part, in which one of the set capturing conditions is a depth of a focus location from a surface of the part based on a measurement depth value indicative of how deep a measurement is to be performed from a surface of the skin part and another one of the set capturing conditions is a set polarization direction which indicates a relationship between a polarization direction of illumination light and a polarization direction of incident light incident on an image sensor, in which the set polarization direction has a value selected from one of a parallel value, an orthogonal value, or a no value, and in which the parallel value indicates that the polarization direction of illumination light is parallel to the polarization direction of incident light, the orthogonal value indicates that the polarization direction of the illumination light is orthogonal to the polarization direction of incident light, and the no value indicates that there is no polarization between the illumination light and the incident light.

8. A non-transitory computer-readable recording medium having recorded thereon a program for causing a computer to execute processes including:

extracting a characteristic amount of a first image;

accumulating learning data, determining when a predetermined amount of learning data has been accumulated, and when a determination result thereof indicates that the predetermined amount of learning data has been accumulated generating a discriminator based on the accumulated learning data, said discriminator being identification information for identifying a part of a living body on the basis of the characteristic amount;

specifying the part of the living body within the first image on the basis of the extracted characteristic amount of the first image capturing skin of the living body and the learned identification information; and setting a number of capturing conditions under which a second image indicating a state of the skin of the part is captured in response to the specified part, in which one of the set capturing conditions is a depth of a focus location from a surface of the part based on a measurement depth value indicative of how deep a measurement is to be performed from a surface of the skin part and another one of the set capturing conditions is a set polarization direction which indicates a relationship between a polarization direction of illumination light and a polarization direction of incident light incident on an image sensor, in which the set polarization direction has a value selected from one of a parallel value, an orthogonal value, or a no value, and in which the parallel value indicates that the polarization direction of illumination light is parallel to the polarization direction of incident light, the orthogonal value indicates that the polarization direction of the illumination light is orthogonal to the polarization direction of incident light, and the no value indicates that there is no polarization between the illumination light and the incident light.

9. An image processing system comprising:

a capturing device; and an image processing device, wherein the image processing device is configured to operate as:

a characteristic analysis unit configured to extract a characteristic amount of a first image;

a learning unit configured to accumulate learning data, to determine when a predetermined amount of learning data has been accumulated, and when a determination result thereof indicates that the predetermined amount of learning data has been accumulated to generate a discriminator based on the accumulated learning data, said discriminator being identification information for identifying a part of a living body on the basis of the characteristic amount;

a specifying unit configured to specify the part of the living body within the first image on the basis of the characteristic amount of the first image of skin of the living body captured by the capturing device extracted by the characteristic analysis unit and the identification information learned by the learning unit; and a setting unit configured to set, on the capturing device, a number of capturing conditions under which a second image indicating a state of the skin of the part is captured in response to the specified part, in which one of the capturing conditions set by the setting unit is a depth of a focus location from a surface of the part based on a measurement depth value indicative of how deep a measurement is to be performed from a surface of the skin part and another one of the capturing conditions set by the setting unit is a set polarization direction which indicates a relationship between a polarization direction of illumination light and a polarization direction of incident light incident on an image sensor, in which the set polarization direction has a value selected from one of a parallel value, an orthogonal value, or a no value, and in which the parallel value indicates that the polarization direction of illumination light is parallel to the polarization direction of incident light, the orthogonal value indicates that the polarization direction of the illumination light is orthogonal to the polarization direction of incident light, and the no value indicates that there is no polarization between the illumination light and the incident light.

* * * * *